United States Patent [19]

Link

[11] 4,154,238

[45] May 15, 1979

[54] APPARATUS AND PROCESS USING SECOND DERIVATIVE OF OSCILLOMETRIC WAVEFORM FOR PRODUCING SPHYGMOMETRIC INFORMATION

[75] Inventor: William T. Link, Berkeley, Calif.

[73] Assignee: American Optical Corporation, Southbridge, Mass.

[21] Appl. No.: 754,133

[22] Filed: Dec. 27, 1976

[51] Int. Cl.$^2$ ............................................. A61B 5/02
[52] U.S. Cl. .................................................. 128/681
[58] Field of Search ................ 128/2.05 A, 2.05 C, 128/2.05 D, 2.05 E, 2.05 Q, 2.05 M, 2.05 Z

[56] References Cited

U.S. PATENT DOCUMENTS

| 3,814,083 | 6/1974 | Fletcher et al. | 128/2.05 A |
|---|---|---|---|
| 3,885,551 | 5/1975 | Massie | 128/2.05 A |
| 3,903,872 | 9/1975 | Link | 128/2.05 A |
| 3,939,824 | 2/1976 | Arneson et al. | 128/2.05 A |
| 3,985,123 | 10/1976 | Herzlinger et al. | 128/2.05 A |

FOREIGN PATENT DOCUMENTS 2219045  10/1973  Fed. Rep. of Germany ...... 128/2.05 Z

OTHER PUBLICATIONS

Chungcharoen, D. "Genesis of Korotkoff Sounds", Amer. Jrnl. Physiology, vol. 207, No. 1, 7/64, pp. 190-194.
Guyton, A. C., "Medical Physiology", W. B. Saunders Co., Philadelphia 1971, pp. 305-306.
Graf, R. F., "Modern Dictionary of Electronics", H. W. Sams Co., Indianapolis 1970, p. 483.
George, M., et al., "Measurement of the Maximum Rate of Rise of Aortic BP in Man", Med. Research Engr. 4th Qtr., 1967, pp. 21-24.,
Berne, et al., "Cardiovascular Physiology", Mosby Co., St. Louis, 1972, p. 99, (definition).
Ray, C. D., "Medical Engineering", Year book Publishing, Chicago, 1974, pp. 153-154.
Winter, Z., et al. "A Simple Cardiac Contractility Computer", Med. & Biol. Engr., 9/73, pp. 560-568.
Angelakos, E. T., "Semi-Conductor Pressure Microtransducers for Measuring V,A of Ventricular Pressures", Amer. Jrnl. Med. Elec., 9-10/64, pp. 266-270.

Primary Examiner—Robert W. Michell
Assistant Examiner—Francis J. Jaworski
Attorney, Agent, or Firm—Jeremiah J. Duggan; Stephen A. Schneeberger

[57] ABSTRACT

An improved method and apparatus for determining blood pressure in a system employing a variable pressure cuff and having means for sensing a quantity comprising the sum of applied cuff pressure and a component representative of pulsatile pressure in a blood vessel, a particular time derivative of at least the fluctuating component of the quantity is obtained and utilized for determining blood pressure. More specifically, the particular time derivative comprises the second (or greater) derivative and it is analyzed to determine at what applied pressure it first and last crosses a negative threshold value, those pressures then being indicated as diastolic and systolic pressure depending on whether applied pressure is increased or decreased. The threshold value may be dynamically determined.

15 Claims, 5 Drawing Figures

APPARATUS AND PROCESS USING SECOND DERIVATIVE OF OSCILLOMETRIC WAVEFORM FOR PRODUCING SPHYGMOMETRIC INFORMATION

BACKGROUND OF THE INVENTION

The invention relates generally to the apparatus and method for noninvasively producing sphygmometric information by analysis of an oscillometric waveform.

The prior art is replete with devices for measuring the blood pressure of a living subject. The simplest and oldest device is a pressurizable cuff used in combination with a mercury manometer which reads the pressure in the cuff and a stethoscope which is used to listen to Korotkoff sounds. More complicated methods and apparatus based on the same principles of listening to the Korotkoff sounds replace the mercury manometer with a mechanical or electromechanical pressure gauge and utilize microphonic detection of the Korotkoff sounds which are amplified electrically. In another advanced method of measuring blood pressure, the distance of a blood pressure cuff to the wall of an artery is actually determined by measuring Doppler shifts of sound waves reflected by the artery. The distance to the artery varies as a function of pressure within the somewhat pliable walls of the artery. Certain multicuff techniques have also been employed and of course, intrusive devices have also been inserted directly into blood vessels to make direct blood pressure measurements.

The methods based on listening to Korotkoff sounds are inherently somewhat inaccurate for measuring diastolic pressure since the human or electromechanical listening must distinguish when a sound fades out. Further, the Korotkoff technique does not work well on newborn patients, obese patients and those patients suffering from shock or hypertension. The method based on doppler shifts, in addition to requiring expensive apparatus, is sensitive to the positioning of the measuring apparatus relative to the artery and requires a coupling gel. The intrusive methods are somewhat painful and require the attention of a trained medical technician. The multicuff techniques suffer from the requirement for multiple nonstandard cuffs and are somewhat prone to artifacts.

In addition to the aforementioned techniques, oscillometric techniques have been developed in which a pressure transducer associated with an inflatable pressure cuff provides an oscillatory signal representative of the pulsatile pressure fluctuation sensed by the pressure cuff as a function of volumetric changes in the embraced blood vessel. One type of oscillometric technique disclosed in U.S. Application Ser. No. 578,047, filed May 15, 1975 and now U.S. Pat. No. 4,009,709 by Link, et al. for Apparatus and Process for Determining Systolic Pressure, and incorporated herein by reference, relies on the amplitude of the oscillatory pulsations to provide an indication of systolic and/or diastolic pressure, however these techniques may be improved upon by the present invention particularly in the presence of various artifacts.

Recently a technique of waveform analysis of the oscillatory signal has been developed which provides superior results in identifying a patient's diastolic blood pressure. This technique is described in greater detail in U.S. Pat. No. 3,903,872 issued Sept. 9, 1975 to W. T. Link for Apparatus and Process for Producing Sphygmometric Information, and is incorporated herein by reference. In that technique, a pulsating signal representative of the sum of the applied pressure of the cuff and the sensed pulsatile pressure of the embraced blood vessel is differentiated. The resulting time derivative signal is evaluated at a specific time in a pulse (on the blood pressure waveform), and the time derivative is seen to go through a (negative) maximum value when the applied cuff pressure is approximately equal to the undistorted arterial pressure at that specific time within the blood pressure waveform of the time derivative maximum proximate to diastole in each heart beat was found to correspond with the diastolic pressure of the blood vessel.

While the technique disclosed in the aforementioned patent provides a powerful and significant advance in the art of sphygmomanometry, it requies relatively expensive apparatus to interpret the waveform and remains somewhat prone to interference from certain artifacts, though to a lesser degree than most earlier mentioned techniques.

Accordingly, it is a principle object of the present invention to provide an apparatus and method for relatively inexpensively and accurately analyzing oscillometric waveforms to provide an indication of the physical condition, and particularly the diastolic and/or systolic blood pressures of a living test subject.

An apparatus and a process for satisfying the foregoing and other objects is disclosed into the following.

SUMMARY OF THE INVENTION

The apparatus and process are based upon the discovery that if pressure applied by a cuff adjacent a blood vessel is plotted against a second time derivative of the observed cuff pressure including the pulsatile effects of the embraced blood vessel, when the applied cuff pressure is approximately between the diastolic and systolic pressures of the blood vessel there exists a negative spike in the second derivative, which negative spike essentially disappears approximately at the applied cuff pressures corresponding respectively with diastolic and systolic pressure. Further, use of the second derivative minimizes artifact problems, particularly low frequency artifacts as from certain muscle activity and the like.

The invention comprises an apparatus for producing information indicative of the physical condition of a living test subject comprising means for converting a quantity proportional to a sum comprising a time dependent fluctuating component representative of the pulsatile pressure within a blood vessel plus a differable (selectively changeable) pressure aplied externally adjacent the blood vessel into a representation of a second time derivative of the quantity and means for analyzing changes in the representation of the second derivative induced by differing (selectively changing) the applied pressure to produce an output indicative of the physical condition of the living test subject. Preferred means for accomplishing the analyzing comprise a means for determining whether or not a negative portion of the second time derivative exceeds a threshold value and further means for identifying when the detected negative second time derivative first and/or last exceeds the negative threshold value such that the applied pressure substantially corresponding therewith may produce an output indicative of the diastolic or systolic pressure of the blood vessel as a function of whether the applied pressure was increasing or decreasing when the change in indication occurred.

In the preferred embodiment of the invention, the applied pressures corresponding with diastolic and systolic pressure of the blood vessel are seen to occur substantially at the first and last instances of the second time derivative negatively exceeding a negative threshold of predetermined voltage magnitude for successive pulses measured over an applied pressure range which includes the diastolic and systolic pressures. Whether a first negative second time derivative exceeding the threshold is indicative of diastolic pressure or indicative of systolic pressure is a function of the direction in which the applied pressure is changed. For instance, for an increasing applied pressure the first negative second time derivative to exceed the threshold is substantially indicative of diastolic pressure and the last is substantially indicative of systolic pressure. The threshold may be determined in a dynamic manner which requires the real-time data to be stored. The time-sense direction in which the subsequent analysis is conducted is optional and the above use of the terms "first" and "last" refer to the real-time acquisition of pressure data.

The invention further comprises a method for producing information indicative of the physical condition of a living test subject. The method comprises converting a quantity proportional to a sum comprising a time dependent fluctuating component representative of the pulsatile pressure within a blood vessel, plus a differable (selectively changeable) pressure applied externally adjacent the blood vessel into a representation of the second time derivative of the quantity and analyzing (preferably electronically) changes in the representation of the second time derivative induced by selectively changing the applied pressure to produce an output indicative of the physical condition of a living test subject. Specifically, the analyzing technique comprises identifying when the negative spike of the second derivative first or last negatively exceeds a threshold value, the applied pressure to which such determination corresponds being indicative substantially of diastolic or systolic pressure as a function of the direction in which the applied pressure is changed.

In a preferred embodiment of the pressure the second derivative is compared with a dynamically determined threshold of small or minimum negative magnitude to ascertain the existence or nonexistence of a negative spike exceeding the threshold.

DETAILED DESCRIPTION OF THE PREFERRED EMBODIMENTS

Figure 1:
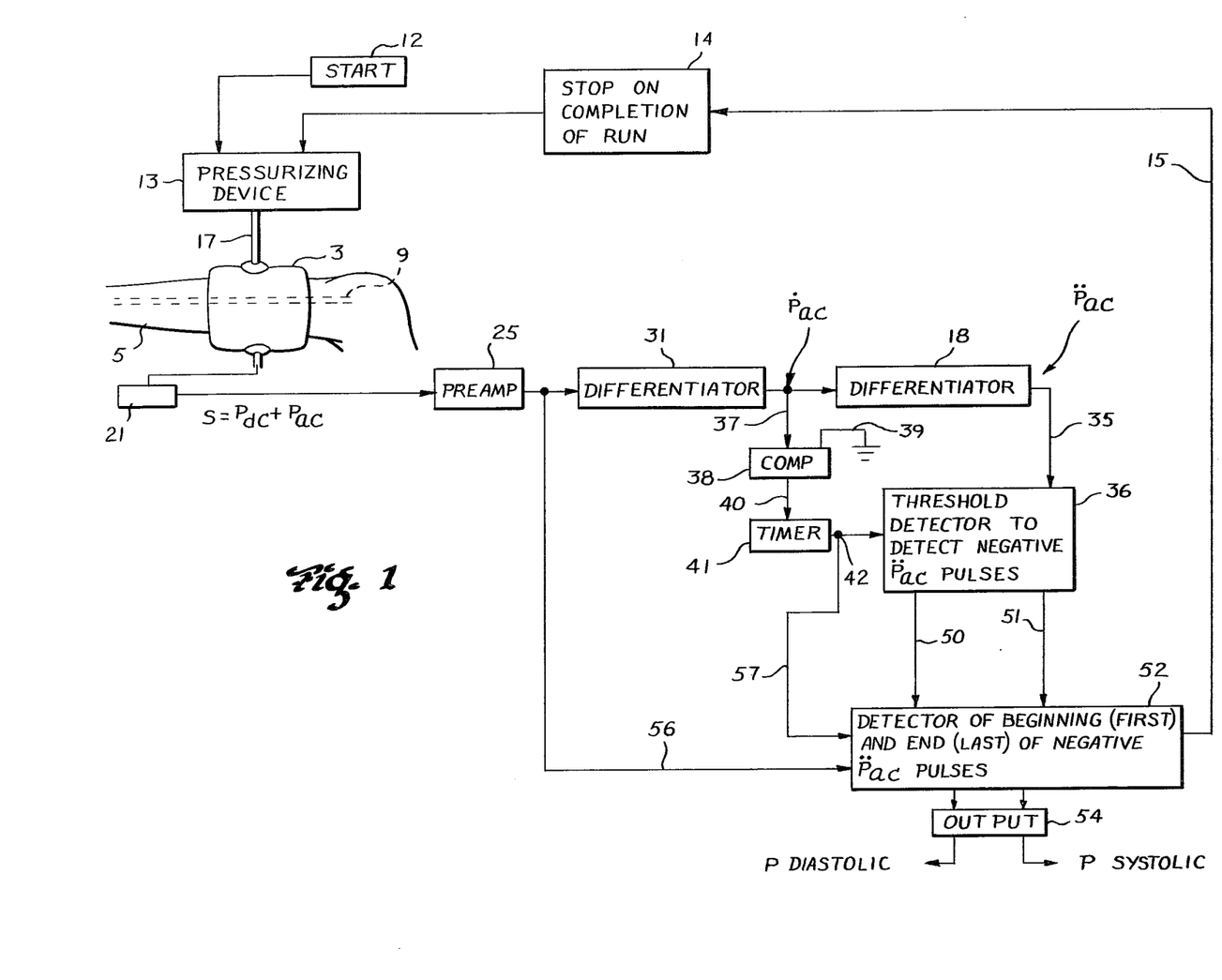
FIG. 1 is a block diagram illustrating the apparatus and process of the present invention in combination with blood pressure measuring equipment.

Referring now to the Figures, and in particular initially to FIG. 1, the preferred embodiments of the invention can be better understood. Means for applying a differable pressure adjacent a blood vessel, said pressure applying means comprising a blood pressure measuring means, in particular a cuff 3 is shown in position about an arm 5 containing an artery 9 therein. The cuff 3 can be a typical blood pressure cuff such as those utilized when one is making use of a stethoscope to hear Korotkoff sounds. Also a part of said pressure applying means along with the cuff is the pump or pressurizing device 13, which can be a simple rubber bulb or it can be a powered pump, acting through the tubing 17. As illustrated, device 13 comprises a powered pump, with pressurizing operation being initiated by actuation of start switch 12 and being terminated by manual or automatic actuation of stop switch 14. Automatic actuation of stop switch 14 may be provided by a signal appearing on line 15 appearing either at a predetermined pressure level or, as in the illustrated embodiment, when sufficient data has been collected for determining a particular patient's diastolic and systolic pressures.

The pressure resulting in the cuff is the sum of the differable pressure supplied by the pressurizing device 13 and a pulsating pressure due to the time-dependent pulsatile pressure surges within the artery, this sum being represented as S in FIG. 1. The cuff pressure is measured by the pressure transducer 21 or by other convenient means. Although the signal S from transducer 21 comprises a sum of the applied pressure and the pulsatile pressure, it should be noted that the applied pressure (designated $P_{dc}$) is many times greater than the pulsatile pressure (designated $P_{ac}$) and accordingly, the value of S is substantially equal to the pressure applied by cuff 13.

The output S of the pressure transducer 21 is preamplified by preamplifier 25 and is then converted to first and second time derivatives respectively by serial passage through differentiator 31 and differentiator 18 respectively. As a practical matter, the differentiator 31 serves to filter out the applied pressure portion of the pressure measured by the transducer 21 whereby the resulting first time derivative is substantially the first time derivative of the pulsating pressure representative of the time dependent pulsatile pressure surges within the artery, and is accordingly represented as $\dot{P}_{ac}$ (or simply $\dot{P}$). Similarly, the differentiation of the $\dot{P}_{ac}$ signal by the secondary differentiator 18 results in the second time derivative of the pulsatile ($P_{ac}$) component of the sensed pressure and is accordingly represented by $\ddot{P}_{ac}$. It will be appreciated that the first derivative signal $\dot{P}_{ac}$ is representative of the slope of the pulsatile pressure $P_{ac}$. Further, the second time derivative $\ddot{P}_{ac}$ is representative of the rate of change of slope of the pulsatile pressure $P_{ac}$.

Figure 2:
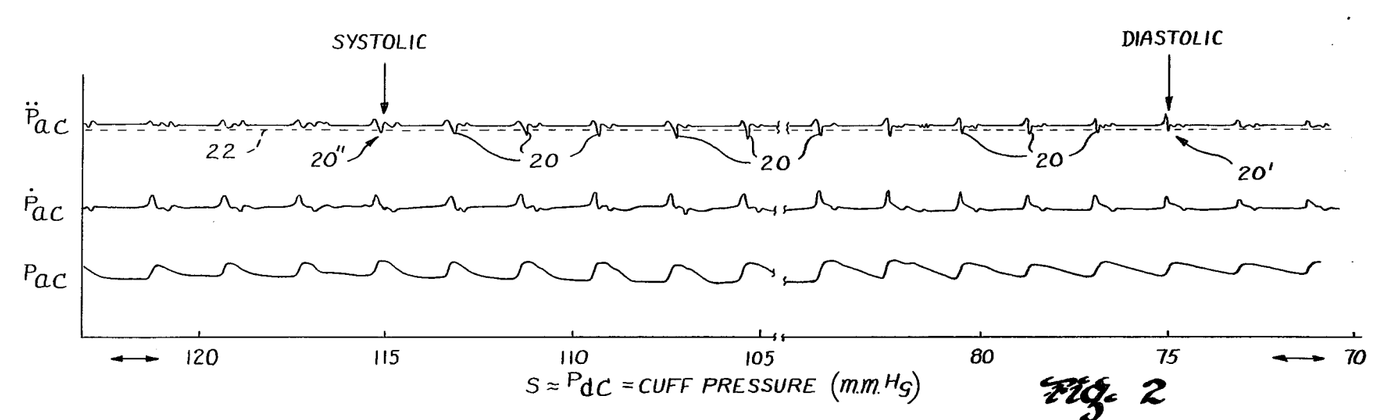
FIG. 2 is a waveform diagram illustrating the $P_{ac}$, $\dot{P}_{ac}$ and $\ddot{P}_{ac}$ waveforms as a function of cuff pressure.
Figure 3:
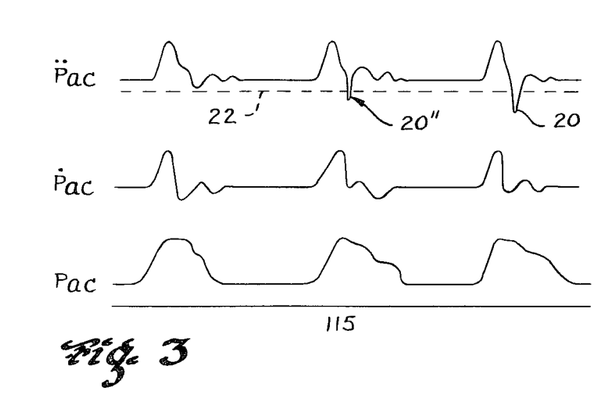
FIG. 3 is an enlarged view of a portion of the several waveforms of FIG. 2 illustrating the transition from an applied pressure beyond the diastolic-systolic pressure range to one within that range.

Referring presently to FIGS. 2 and 3, the respective $P_{ac}$, $\dot{P}_{ac}$ and $\ddot{P}_{ac}$ waveforms are illustrated as a function of the pressure sum S, or essentially the differable applied pressure of cuff 3. It is well known that diastolic and systolic pressure measurements may be taken either by increasing the pressure applied to cuff 3 or by decreasing that pressure from a previously elevated level. Accordingly, the waveforms of FIG. 2, if read from left to right, are appropriate for a declining applied pressure ramp and, if read from right to left, are applicable to an increasing applied pressure ramp. In either event, the patient's systolic pressure would obviously always appear at a higher applied pressure than for the diastolic pressure. By applying the techniques of the invention, the patient's systolic pressure illustrated in FIG. 2 was found to be about 115 mm of mercury (Torr) and the diastolic pressure was found to be about 75 mm of mercury (Torr).

As the pressure applied by cuff 3 is decreased, the $P_{ac}$ signal is seen to increase in amplitude until a point somewhere between systolic and diastolic pressure whereupon it begins a decrease in amplitude. More importantly, it was discovered that the $P_{ac}$ waveform developed or acquired a relatively sharp or acutely angled left shoulder at the systolic pressure, the sharpness or angle of this shoulder becoming more acute as the mid range of systolic-diastolic pressure was reached and becoming less acute as the diastolic pressure was approached until, at or essentially following diastolic pressure the left shoulder of the waveform was no longer acute and had returned to the generally rounded shape seen prior to systolic pressure.

Although the process resulting in the sharp or acute left corner of the pulsatile waveform for each heartbeat in the diastolic-systolic range is poorly understood, it does permit an analysis of the second time derivative thereof ($\ddot{P}_{ac}$) which is capable of relatively accurately identifying the patients systolic and diastolic pressures. In fact, using the techniques of the invention, the determined systolic pressure corresponds almost exactly with that determined by the first Korotkoff sound, and the diastolic pressure is determined to be somewhat lower than that measured by Korotkoff fourth phase sounds and essentially equal to that measured by Korotoff fifth phase sounds.

A close observation of the $\ddot{P}_{ac}$ waveform reveals that as the applied pressure is decreased and the patient's systolic pressure is approached, there begins a small negative spike which becomes measurably noticeable at the systolic pressure and continues to increase negatively in magnitude as the pressure is further dropped through the systolic-diastolic range to a maximum in mid-range whereafter it decreases in magnitude to the point at which it is no longer measureable, substantially at the pressure corresponding with diastolic pressure. This feature of the $\ddot{P}_{ac}$ waveform occurs because of the relatively sharp corner or acute angle appearing throughout the diastolic-systolic range and essentially beginning and ending therewith. FIG. 3, which represents an enlarged and somewhat exaggerated portion of FIG. 2 at the point of systolic pressure, more clearly illustrates the foregoing observations. The negative spikes or pulses 20 in the second time derivative waveform $\ddot{P}_{ac}$ result from the down-slope of the trailing edge of the $\dot{P}_{ac}$ waveform, which in turn results from a negative change in the slope of the $P_{ac}$ waveform. A marked change in the slope of the $P_{ac}$ waveform occurs at the end of the systolic rise at which time the slope either becomes negative or at least less positive. If this change in the slope of the $P_{ac}$ waveform is abrupt or provides a sharp shoulder, the abruptness is reflected in a steep negative slope to the trailing edge of the $\dot{P}_{ac}$ waveform which accordingly increases the negative magnitude of the $\ddot{P}_{ac}$ waveform.

Figure 4:
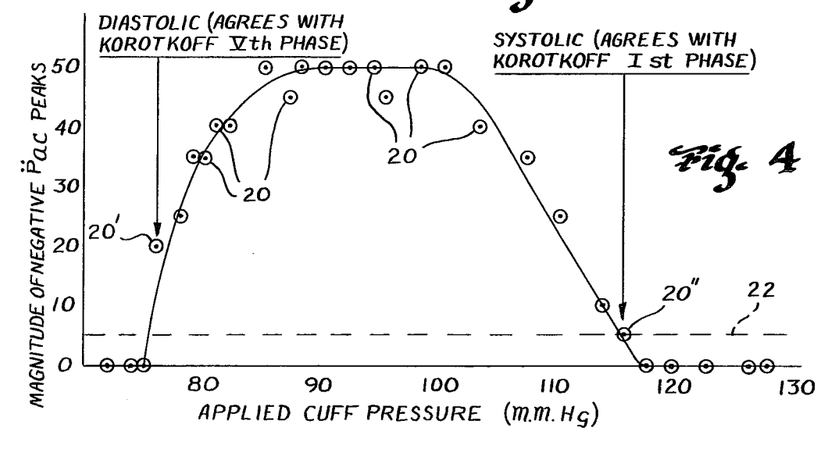
FIG. 4 illustrates a plot of the magnitude of the negative portion of the second derivative as a function of applied cuff pressure.

In order to identify the points of systolic and diastolic pressure, there is established a negative threshold level represented by line 22 in FIGS. 2, 3 and 4. Threshold 22 is a signal voltage value or magnitude which is only slightly below or negative relative to the zero baseline voltage of the $\ddot{P}_{ac}$ waveform. More specifically, threshold 22 may be selected to be a predetermined fraction of the negative voltage of the most negative going spike 20 in the series thus providing a dynamic threshold 22. For instance, threshold 22 might be selected to have a negative voltage value which is about 1/7 or 1/10 of the negative voltage to which the maximum negative going pulse 20 extends. Although a predetermined threshold might be used, the dynamic threshold avoids the problem of a fixed threshold in the presence of $\ddot{P}_{ac}$ signals which may differ in amplitude from patient to patient or as a function of the situation of the moment.

Referring to FIG. 4, there is illustrated a plot of the magnitude of the negative $\ddot{P}_{ac}$ peaks in arbitrary units as a function of cuff pressure. From this plot it will be noted that the negative magnitude of the $\ddot{P}_{ac}$ wave signal for the blood pressure pulses beyond the diastolic-systolic range have a value which is substantially equal to zero and that the mid-range negative peak magnitudes correspond with the value of 50. Further it will be noted that the negative $\ddot{P}_{ac}$ peak of smallest non-zero magnitude occurs near the systolic pressure and has a magnitude of about 5 units. Accordingly, by establishing a dynamic threshold 22 whose magnitude is about 1/10 that of the maximum negative $\ddot{P}_{ac}$ peak, the points of diastolic and systolic pressure are identified with a good degree of accuracy.

Thus, by identifying the applied cuff pressures substantially at which the $\ddot{P}_{ac}$ spikes negatively first and last exceed threshold 22, such pressures may then be outputed as diastolic and systolic pressures depending upon the direction in which the cuff pressure is being changed. The negative $\ddot{P}_{ac}$ peaks 20' and 20" correspond substantially with the diastolic and systolic pressures respectively.

Figure 5:
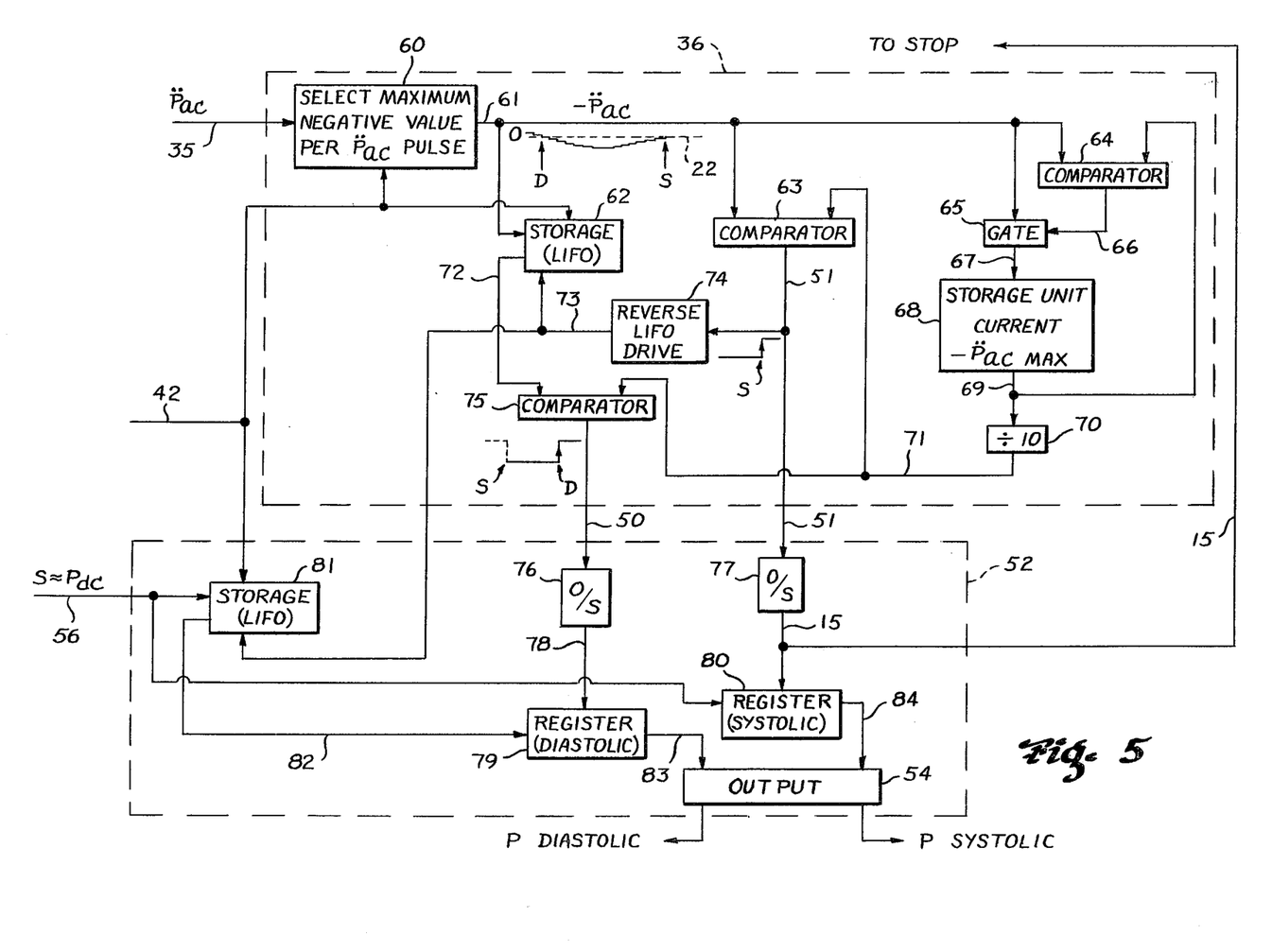
FIG. 5 illustrates a portion of the block diagram of FIG. 1 in greater detail.

Referring back to FIG. 1 and to FIG. 5, it will be appreciated that the apparatus might be fully implemented in an analog form or alternatively entirely or partially in a digital form. In a preferred arrangement the preamplifier 25, differentiator 31, and differentiator 18 are preferably analog circuits with most of the remaining circuitry exclusive of the final output being digital and utilizing a properly programmed microprocessor. The following discussion of the signal processing circuitry will be generally of a functional nature but the implementation thereof either in hardware or software will be obvious to one of ordinary skill in the art. Similarly, circuitry for converting between the analog and digital forms is inferred rather than specifically illustrated and discussed. The $\ddot{P}_{ac}$ waveform appearing at the output of differentiator 18 is extended via line 35 to waveform analysis circuitry comprised generally of threshold detecting means 36 for determining whether or not the negative $\ddot{P}_{ac}$ pulses exceed the threshold 22 earlier mentioned and state-change or transition detection circuitry 52 which responds to the output of threshold detection circuitry 52 to indicate which of a series of $\ddot{P}_{ac}$ pulses first and/or last negatively exceed the threshold as a function of differing the applied pressure across a range. The applied pressure ($S \approx P_{dc}$) corresponding with a detected state-change is then read out or displayed by a suitable output device 54.

A better understanding of some of the following functionally described, nonillustrated apparatus may be obtained from the aforementioned U.S. Pat. NO. 3,903,872 and the aforementioned U.S. Pat. No. 4,009,709. The $\dot{P}_{ac}$ signal of the output of differentiator 31 is conveniently used for timing purposes and is extended by conductor 37 to the input of comparator 38. The other input to comparator 38 is connected by conductor 39 to a zero reference voltage such as ground. In this way, the output of comparator 38 remains at zero so long as the first derivative $\dot{P}_{ac}$ waveform is below a zero reference line and switches to unity or one when $\dot{P}_{ac}$ goes positive during the systolic rise of each blood pressure pulse. The output of comparator 38 represented by line 40 is extended to the input of a timer 41 and the zero-to-unity transitions serve to restart the timer 41.

An output from timer 41, represented by line 42, is extended to the threshold detection circuitry 36 and transition detection circuitry 52 for controlling intra and inter pulse analysis timing. Typically, the $\ddot{P}_{ac}$ waveform appearing on line 35 will be converted from analog to digital form at a rate which may typically provide some 50-150 samples of the waveform between successive heart beats. In order to reduce the effects of artifacts, several successive intrapulse samples may be averaged and the continuously updated average then utilized as the $\ddot{P}_{ac}$ signal extended on line 35 to optional circuitry 60 which is operative in a known manner to sample and hold the maximum negative value attained by each blood pressure pulsation. This per-pulse negative maximum may then be determined once for each pulse and utilized as the representative negative value for that pulse until replaced by a new value at the next pulse. By performing this function at this location, the need for doing so at plural subsequent positions is avoided.

Referring to FIG. 5, the per pulse maximum negative values determined by circuit 60 are extended, as represented by line 61, to the appropriate inputs of a last-in, first-out storage unit 62, comparator 63, comparator 64, and gate 65. Gate 65 and comparator 64 are utilized to dynamically determine the threshold value represented by line 22 in FIGS. 2-4. The signal appearing on line 61 are represented by the waveform illustrated thereunder and have only negative values, those values being minimal or less than the threshold 22 beyond each end of the diastolic-systolic pressure range, and being significant and equal to or exceeding the threshold within the diastolic-systolic pressure range.

The threshold level represented by line 22 may be of a magnitude which is about 1/10 the peak negative magnitude experienced by the $-\ddot{P}_{ac}$ signals in the midrange between the diastolic and systolic pressures. In determining this threshold level, the comparator 64 as represented by line 66, controls gate 65. The gate 65 serves, as represented by line 67, to load a selected value of the $-\ddot{P}_{ac}$ pulses into storage unit 68. The value of the quantity being stored in storage unit 68 is supplied to the comparator 64, as represented by line 69. Within comparator 64, stored tentative previous representations of the maximum negative value attained by the several preceding $\ddot{P}_{ac}$ pulses are compared with current values of said quantity introduced, via line 61, into the comparator 64. When a value of the $-\ddot{P}_{ac}$ quantity supplied to the comparator 64, as represented by line 61, is greater than the quantity tentatively stored in the storage unit 68, then gate 65 is activated by the comparator 64, as represented by line 66, and the larger negative value of the quantity replaces the tentative maximum value in storage unit 68.

The tentative maximum value of the quantity in storage unit 68 is introduced, as also represented by line 69, into a divide-by-ten unit 70 wherein it is divided by a factor of ten. The output of divide-by-ten unit 70, as represented by line 71, represents a value which is 1/10 the tentative maximum stored in unit 68. The tentative maximum stored in unit 68 will normally continue to increase until a final or steady-state maximum somewhere in the middle of the diastolic-systolic range. Similarly, the 1/10 maximum value represented by line 71 will also attain and maintain a steady maximum when the middle of the diastolic-systolic range is reached.

The threshold signal represented by line 71 is extended to an input of comparator 63 for comparison with the $-\ddot{P}_{ac}$ signals appearing on line 61 at the other input of the comparator. Comparator 63 is of the type whose output, as represented by line 51, is at a logic zero level so long as the signal on line 61 negatively exceeds the magnitude of the threshold signal on line 71. In the illustrated embodiment, an increasing applied pressure has been assumed and accordingly, the output of comparator 72 will remain a logic zero throughout the lower portion of the pressure ramp including the diastolic pressure and will change to the logic one state only when the negative quantity appearing on line 61 is of lesser magnitude than the threshold on line 51, as occurs at the systolic pressure. At systolic pressure, the relative magnitudes of the inputs of comparator 63 are reversed and the output represented by line 72 steps to a logic one, as represented by the arrow on the waveform adjacent thereto, the positive-going step then being utilized to provide an indication of the occurrence of systolic pressure as will be hereinafter further described.

It will be appreciated that the determination of a threshold value on line 71 at the lower applied pressure corresponding with the diastolic pressure is not at that time the appropriate "steady state" magnitude represented as 1/10 the maximum negative value attained over the full pressure range. Therefore, the search for the applied pressure at which the $-\ddot{P}_{ac}$ signal first negatively exceeded the "steady state" threshold may not be conducted until after the real-time occurrence of diastolic pressure and the final determination of the threshold. For that reason, it is necessary to store both the $-\ddot{P}_{ac}$ signals appearing on line 61 and the applied pressure values appearing on line 56 over the full diastolic-systolic pressure range for a subsequent "look back" to determine the diastolic pressure.

The storage unit 62 if of the last-in, first-out type and may comprise a push-down stack or the like. Real-time data appearing on line 61 is sequentially entered into storage unit 62 by the timing pulses appearing on line 42. The data-length of the storage unit 62 is at least sufficient to extend the full diastolic-systolic range. In the illustrated embodiment, the detection of the systolic pressure by comparator 63, as represented on line 61, serves to generate a signal on line 15 which is extended to the completion-of-run circuitry 14 for terminating further increase in the cuff pressure and initiating a rapid pressure bleed. Accordingly, the last or next-to-last signal entered in storage unit 62 will comprise the negative $\ddot{P}$ signal commensurate with an indication of systolic pressure, and a signal toward "other end" of the storage unit 62 will be indicative of the diastolic pressure. At this point the "steady-state" threshold signal on 71 will of course have been determined and the data in storage unit 62 is readout in reverse, as represented by line 72, such that the point of diastolic pressure may then be determined. This reverse readout of data in storage unit 62 is controlled by drive signals represented by line 73 provided by the reverse drive circuitry 74 which is initiated by the positive step appearing on line 51 of comparator 63.

The $-\ddot{P}_{ac}$ data readout of storage unit 62 via line 72 is extended to an input of the comparator 75, the other input of that comparator being provided by the threshold signal established on line 71. Because the data of storage unit 62 is being readout in reverse beginning shortly after the real-time occurrence of the systolic pressure as recognized by comparator 63, the data which is extended to comparator 75 will essentially immediately be the $-\ddot{P}_{ac}$ signal commensurate with the systolic pressure and will proceed backwardly in time through the diastolic-systolic range to at least the signal corresponding with diastolic pressure. Comparator 75 is of the type similar to comparator 63 and remains in a logic zero state so long as the data appearing on line 72 negatively exceeds the magnitude of the threshold signal appearing on line 71. The output of comparator 75, as represented by line 50, will step to the logic one state as illustrated in the waveform adjacent thereto when, at diastolic pressure, the $-\ddot{P}_{ac}$ signal is of lesser magnitude than the threshold signal. It will be further noted that the output 50 of comparator 75 may initially be at a logic one level and immediately go the logic zero level at systolic pressure, particularly if the final data stored in unit 62 slightly overshoots the systolic pressure. However, in the illustrated embodiment, this is of no consequence because positive-going edges of the outputs of comparators 75 and 63 are utilized for timing rather than particular logic levels.

Referring now to the transition or state-change detection circuitry 52, the outputs 50 and 51 of comparators 75 and 63 respectively are extended to the triggering inputs of one-shots 76 and 77 respectively. The one-shot 76 is responsive to the positive step in the output of comparator 75 occurring at diastolic pressure to generate an output pulse, as represented by line 78, for controlling data entry into register 79. Similarly, one-shot 77 is responsive to the positive-going step in the output of comparator 63 at the systolic pressure to generate an output pulse, as represented by line 15, which not only terminates the change in pressure of cuff 3 but also controls the entry of data into register 80. It will be appreciated that the pulse outputs from one-shots 77 and 76 correspond respectively with the real-time occurrence of the systolic pressure and with the delayed-time occurrence of diastolic pressure. Furthermore, it will be appreciated that the positive-going step outputs of the comparators 75 and 63 might be used directly to control the input of data 79 and 80 and might then be considered as providing the detection of the aforementioned stage-change.

As earlier noted, although the diastolic pressure occurs in real-time before the systolic pressure, the data processing cycle is such that the systolic pressure is first recognized and the diastolic pressure subsequently recognized. Accordingly, the signal appearing on line 56 and substantially representative of the applied pressure is extended directly to the data input of register 80 and additionally to the data input of a last-in, first-out storage unit 81. At the end of the real-time increase in applied pressure a pulse, as represented by line 15, is generated for entering the corresponding applied pressure value into register 80, this value being indicative of the systolic pressure.

The LIFO storage unit 81 operates substantially identically with storage unit 62 and accordingly receives input timing signals via line 42 and reverse LIFO drive signals via line 73. The data stored in unit 81 is read out in LIFO fashion and is extended, as represeted by line 82, to the data input of register 79. Thus, the applied pressure value entered in register 79 will correspond with the $-\ddot{P}_{ac}$ value which resulted in the generation of the control pulse 78 corresponding with diastolic pressure.

The outputs of register 79 and 80, as represented by line 83 and 84 respectively, are extended to respective inputs of the output device 54 for read out and/or display. Although in the illustrated instance the systolic pressure value is available before the diastolic pressure value, the output 54 may be controlled to wait until the diastolic pressure value is available before displaying both values. It will be further appreciated that a down-ramping of the applied cuff pressure might have been used, resulting in a corresponding time inversion of the collected data and the processing thereof. Still further, it will be appreciated that the storage unit 62 and 81 might be eliminated and the diastolic and systolic pressure determinations made in the real-time domain if a predetermined fixed threshold value is used, rather than determining such value dynamically, though such arrangement would be subject to the shortcomings which were previously mentioned.

Additional logic and control features not specifically illustrated and described herein might be included to further enhance the performance of the blood pressure monitor. For example, if the $\ddot{P}_{ac}$ signals should exhibit an artifact which, in negative magnitude, fell on the "wrong" side of the threshold 22 there might result an incorrect determinaton of the transition point at which the threshold is crossed, thus resulting in an erroneous determination of diastolic or systolic pressure. In large part, this problem is minimized by averaging the data which is analyzed, however it may be further desirable to analyze several succeeding data points to determine if the transition was indeed a valid one. Correspondingly, a validating or invalidating control signal may be generated and utilized to either validate certain decisions or to invalidate them and continue the analysis until valid data is obtained.

In the instance where the ramp rate of the applied pressure is slow (ie. about 2 mm Hg/sec.) the first and last $-\ddot{P}_{ac}$ peaks 20' and 20" exceeding threshold 22 provide good indication of the diastolic and systolic pressures. However if the pressure ramp rate is significantly faster such that the applied pressure may differ by 5-10 mm Hg or more per pulse, it may be desirable in the interest of improved accuracy to interpolate between the applied pressure values corresponding with the adjacent $\ddot{P}_{ac}$ in which one $\ddot{P}_{ac}$ value exceeds threshold 22 and the other does not. Alternatively, the several $-\ddot{P}_{ac}$ values just exceeding the threshold 22 adjacent a transition might be extrapolated to the threshold, as would also be the commensurate values of applied pressure.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. An apparatus for producing information indicative of the physical condition of a living test subject comprising:

means for applying a selectively changeable pressure to the test subject adjacent a blood vessel;

means for measuring a fluctuating quantity proportional to a sum, said sum comprising a time-dependent fluctuating component representative of the pulsatile pressure within the blood vessel, plus the selectively changeable pressure applied externally adjacent the blood vessel;

means for converting said quantity into a representation of a time derivative of at least the fluctuating component thereof, said time derivative being at least the second time derivative of said fluctuating component;

means for analyzing changes in said representation of said at least second time derivative induced by changing the applied pressure, said analyzing means including means for determining and representing whether or not said at least second time derivative at least attains a particular negative threshold value, and means responsive to a change in the state of said threshold attainment representation as a function of said applied pressure for producing an output corresponding substantially with the applied pressure which results in a respective said state-change and is to a close approximation equal to at least one of either the diastolic or the systolic pressures of the blood vessel of the living test subject as determined by the direction of said state-change as a function of the direction of applied pressure change.

2. The apparatus of claim 1 wherein the change in state of said threshold attainment representation to a representation of the existence of said negative value of said second derivative results in said output being diastolic pressure if said applied pressure is being decreased and being systolic pressure if said applied pressure is being increased, the converse being true where said change in state of said threshold attainment representation is to a representation of nonexistence of said negative value of the second derivative.

3. The apparatus of claim 2 wherein said applied pressure is changeable over a range sufficient to embrace both said diastolic and said systolic pressures of the blood vessel, and said output comprises both of said diastolic and said systolic blood pressures.

4. The apparatus of claim 1 wherein said particular threshold value is a relatively negative minimum magnitude value of said second time derivative.

5. The apparatus of claim 4 wherein said threshold attainment representing means comprise means for dynamically determining said particular threshold value as a function of maximum negative magnitude attained by said second time derivative representation across a continuous range of applied pressures which includes the diastolic and systolic pressures of the blood vessel.

6. The apparatus of claim 5 wherein said dynamically determined threshold value is substantially 1/10 the magnitude of said maximum negative magnitude attained by said second time derivative representation.

7. In an apparatus for producing information indicative of the physical condition of a living test subject, said apparatus including means for applying a selectively changeable pressure to the test subject adjacent a blood vessel and means for measuring a fluctuating quantity proportional to a sum, said sum comprising a time-dependent fluctuating component representative of the pulsatile pressure within the blood vessel, plus the selectively changeable pressure applied externally adjacent the blood vessel, the improvement comprising:

means for converting said quantity into a representation of a time derivative of at least the fluctuating component thereof, said time derivative being at least the second time derivative of said fluctuating component;

means for analyzing changes in said representation of said at least second time derivative induced by changing the applied pressure, said analyzing means including means for determining and representing whether or not said at least second time derivative at least attains a particular threshold value, said threshold value being a fraction of the maximum negative magnitude attained by said second time derivative representation across a continuous range of applied pressures which includes the diastolic-systolic pressures of the blood vessels, and means responsive to a change in the state of said threshold attainment representation as a function of said applied pressure for producing an output corresponding substantially with the applied pressure which results in a respective said state-change and is to a close approximation equal to either the diastolic or the systolic pressures of the blood vessel of the living test subject as determined by the direction of said state-change as a function of the direction of applied pressure change.

8. The apparatus of claim 7 wherein said particular threshold value comprises a minimum relatively negative magnitude of said at least second time derivative.

9. A method for producing information indicative of the physical condition of a living test subject comprising:

applying a selectively changeable pressure to the subject externally adjacent the blood vessel;

measuring a quantity proportional to a sum, said sum comprising a time dependent fluctuating component representative of the pulsatile pressure within the blood vessel, plus the changeable pressure applied externally adjacent the blood vessel;

converting said quantity into a representation of the second time derivative of at least the fluctuating component thereof;

analyzing changes in said representation in said second time derivative induced by changing the applied pressure, said analyzing comprising the steps of determining and representing whether or not said second time derivative at least attains a particular negative threshold value and identifying a change in the state of said representation of threshold attainment in successive pulses as a function of the applied pressure; and producing from said identifying an output corresponding substantially with the applied pressure which results in a respective said state-change and is to a close approximation equal to at least one of either the diastolic or the systolic pressures of the blood vessel of the living test subject as determined by the direction of said state-change as a function of the direction of applied pressure change.

10. The method of claim 9 wherein the state-change of said threshold attainment representation to a representation of the existence of said negative value of the second derivative results in said output being diastolic pressure if said applied pressure is being decreased and being systolic pressure if said applied pressure is being increased, the converse being true where said state-change of said threshold attainment representation is to a representation of nonexistence of said negative value of the second derivative.

11. The method of claim 10 wherein said applied pressure is changed over a range sufficient to embrace both said diastolic and said systolic pressures of the blood vessel whereby said output comprises both of said diastolic and said systolic blood pressures.

12. The method of claim 9 wherein said particular threshold value is a relatively negative minimum magnitude value of said second time derivative.

13. The method of claim 12 wherein said determining and representing threshold attainment comprises dynamically determining said particular threshold value as a function of maximum negative magnitude attained by said second time derivative representation across a continuous range of applied pressures which includes the diastolic-systolic pressures of the blood vessel and comparing said second time derivative representation with said dynamically determined threshold value.

14. In a method for producing information indicative of the physical condition of a living test subject, including applying a selectively changeable pressure to the subject externally adjacent the blood vessel and measuring a quantity proportional to a sum, said sum comprising a time-dependent fluctuating component representative of the pulsatile pressure within the blood vessel, plus the changeable pressure applied externally adjacent the blood vessel, the improvement comprisng:

converting said quantity into a representation of the second time derivative of at least the fluctuating component thereof;

analyzing changes in said representation in said second time derivative induced by changing the applied pressure, said analyzing comprising the steps of determining and representing whether or not said second time derivative at least attains a particular threshold value, said threshold value being a fraction of the maximum negative magnitude attained by said second time derivative representation across a continuous range of applied pressures which includes the diastolic-systolic pressures of the blood vessls, and identifying a change in the state of said representation of threshold attainment in successive pulses as a function of the applied pressure; and producing from said identifying an output corresponding substantially with the applied pressure which results in a respective said state-change and is to a close approximation equal to either the diastolic or the systolic pressures of the blood vessel of the living test subject as determined by the direction of said state-change as a function of the direction of applied pressure change.

15. The method of claim 14 wherein said particular threshold value comprises a minimum relatively negative magnitude of said at least second time derivative.

* * * * *

UNITED STATES PATENT AND TRADEMARK OFFICE
CERTIFICATE OF CORRECTION

PATENT NO. : 4,154,238
DATED : May 15, 1979
INVENTOR(S) : William T. Link

It is certified that error appears in the above-identified patent and that said Letters Patent are hereby corrected as shown below:

In column 2, line 16, delete "requies" and insert "requires";

In column 2, line 29, delete "into" and insert "in";

In column 3, line 42, delete "pressure" and insert "invention";

In column 3, line 43, delete "dynamieally" and insert "dynamically";

In column 7, line 33, delete "signal" and insert "signals".

Signed and Sealed this

Thirtieth Day of October 1979

[SEAL]

Attest:

RUTH C. MASON
Attesting Officer

LUTRELLE F. PARKER
Acting Commissioner of Patents and Trademarks